United States Patent [19]
Allen et al.

[11] Patent Number: 5,036,099
[45] Date of Patent: Jul. 30, 1991

[54] ANHYDROUS, CRYSTALLINE SODIUM SALT OF 5-CHLORO-3-(2-THENOYL)-2-OXINDOLE-1-CARBOXAMIDE

[75] Inventors: Douglas J. M. Allen, New London; Brian T. O'Neill, Westbrook, both of Conn.

[73] Assignee: Pfizer Inc., New York, N.Y.

[21] Appl. No.: 460,137

[22] PCT Filed: Feb. 2, 1987

[86] PCT No.: PCT/US87/00201
§ 371 Date: Jul. 18, 1989
§ 102(e) Date: Jul. 18, 1989

[87] PCT Pub. No.: WO88/05656
PCT Pub. Date: Aug. 11, 1988

[51] Int. Cl.$^5$ .................... A61K 31/40; C07D 409/06
[52] U.S. Cl. ........................................ 514/414; 548/468
[58] Field of Search .......................... 514/414; 548/468

[56] References Cited

U.S. PATENT DOCUMENTS 3,767,653 10/1973 Krapcho ............................. 548/468
4,556,672 12/1985 Kadin ................................. 548/468

FOREIGN PATENT DOCUMENTS 153818 9/1985 European Pat. Off. ........... 514/414

Primary Examiner—Mary E. Ceperley
Attorney, Agent, or Firm—Peter C. Richardson; J. Trevor Lumb; Robert K. Blackwood

[57] ABSTRACT

Anhydrous, crystalline sodium salt of 5-chloro-3-(2-thenoyl)-2-oxindole-1-carboxamide having advantageous properties for formulation as an analgesic or anti-inflammatory agent.

3 Claims, No Drawings

ANHYDROUS, CRYSTALLINE SODIUM SALT OF 5-CHLORO-3-(2-THENOYL)-2-OXINDOLE-1-CARBOXAMIDE

BACKGROUND OF THE INVENTION

The present invention is directed to a novel crystalline anhydrous sodium salt of 5-chloro-3-(2-thenoyl)-2-oxindole-1-carboxamide having advantageous properties for pharmaceutical formulation as an analgesic or antiinflammatory agent.

Kadin, U.S. Pat. No. 4,556,672 has disclosed said 5-chloro-3-(2-thenoyl)-2-oxindole-1-carboxamide, of the formula

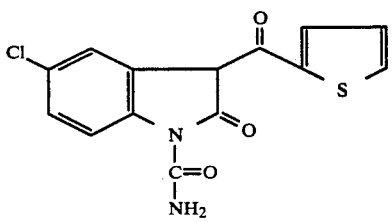

(or a pharmaceutically acceptable salt) as an especially preferred compound for use as an analgesic or antiinflammatory agent. In that disclosure the sodium salt of the compound of the formula (I) was alternatively isolated as a hemihydrate or hydrate. The monohydrate was rendered anhydrous by further drying. We have now determined that several hydrates are formed, generally as mixtures having various morphologies (e.g., amorphous and needle shaped crystals). These various hydrated forms generally have flow and electrostatic properties which make formulation difficult. We have also determined that the anhydrous product obtained by simple drying at elevated temperature and/or reduced pressure is amorphous and hygroscopic. It was therefore highly desirable to find a crystalline form of the sodium salt which might overcome these difficulties.

SUMMARY OF THE INVENTION

We have now found an anhydrous, crystalline form of the sodium salt of 5-chloro-3-(2-thenoyl)-2-oxindole-1-carboxamide which possesses valuable and unobvious properties. Thus, this salt is readily handled and formulated into dosage forms such as capsules. It is not hygroscopic, remaining stable in dosage forms even at 90% relative humidity. When compacted into tablets, it dissolves more rapidly than the hydrated salt.

This advantageous crystalline salt is generally formulated and used as an analgesic according to earlier disclosure of Kadin, cited above, hereby incorporated by reference.

Surprisingly, it is simply prepared by stirring a hydrated form of the sodium salt in acetonitrile at ambient temperature. This transformation has been observed in no other solvent at that temperature, although it does occur less conveniently in refluxing toluene.

DETAILED DESCRIPTION OF THE INVENTION

Once discovered, the present invention is readily carried out. In this process the sodium salt of the compound of the formula (I) is preferably first isolated in the form of its hydrate, which is then simply stirred in acetonitrile to obtain the present advantageous, anhydrous, non-hygroscopic, crystalline sodium salt. The temperature of this transformation in acetonitrile is not critical, but it is conveniently carried out at ambient temperature, avoiding the energy costs of either heating or cooling. The transformation is alternatively, but much less conveniently carried out in toluene with azeotropic removal of water by means of a Dean-Stark trap at the reflux temperature of toluene. Since lower boiling benzene is much less efficient in this process, generally producing anhydrous product which is amorphous, it is believed that use of higher temperatures are critical to the anhydrous crystal formation when the solvent is other than acetonitrile.

The present crystalline salt is characterized by its particular physical properties as noted below. It is generally formulated and used as earlier disclosed by Kadin, cited above. A particular, stable and clinically useful capsule formulation comprising the present salt is exemplified below.

The following examples are given by way of illustration and are not to be construed as limitation of this invention, many variations of which are possible within the scope and spirit thereof.

PREPARATION 1

Hydrated Sodium Salt of 5-Chloro-3-(2-thenoyl)-2-oxindole-1-carboxamide

Title hydrates are prepared according to Example 10 of Kadin, U.S. Pat. No. 4,556,672. Alternatively, 5-chloro-3-(2-thenoyl)-2-oxindole-1-carboxamide (Example 8 of said Kadin; 51.2 g., 0.16 mol) was suspended in 400 ml. $CH_3CN$ at 40° C. Concurrently, $NaHCO_3$ (14.1 g., 0.168 mol) was dissolved in 200 ml. of $H_2O$ and warmed to 40° C. The warm aqueous solution was added to the warm acetonitrile suspension over 20 minutes, during which slight foaming was noted. The resulting solution was stirred at 40° C., treated with 5 g. of decolorizing carbon, stirred at 25° C. for 30 minutes and filtered with 50 ml. of 1:1 $CH_3CN:H_2O$ for wash. The combined filtrate and wash was concentrated in vacuo over a steam bath as the acetonitrile was displaced with 200 ml. of water to a final volume of about 500 ml., cooled to 25° C. and a first crop recovered by filtration. The solids were washed with 50 ml. of water. The combined mother liquor and wash was stripped to 400 ml. to yield a second crop. After drying under air, the first crop weighed 35.76 g. (6.4% water) and the second crop weighed 16.77 g. (6.2% water), a 90% yield corrected for $H_2O$ content. The water level calculated for the monohydrate is 5.0%. Differential scanning calorimetry on these two crops showed 4 endotherms (at about 110, 150, 237 and 255).

EXAMPLE 1

Anhydrous, Crystalline Sodium Salt of 5-Chloro-3-(2-thenoyl)-2-oxindole-1-carboxamide Hydrated sodium salt of 5-chloro-3-(2-thenoyl)-2-oxindole-1-carboxamide (52.5 g., prepared according to the alternative method of Preparation 1) was stirred at ambient temperature in 52.5 ml. of $CH_3CN$. Title product was recovered by filtration, with 50 ml. $CH_3CN$ wash, and dried at 55° C. in vacuo to yield 46.7 g.(95%) of title product; crystalline under the polarizing microscope; differential scanning calorimetry over the range 50°–300° C. shows a single sharp endotherm at 255°±2° C. Anal. Calcd. for $C_{14}H_8ClN_2O_3SNa$: C, 49.06; H, 2.35; N, 8.18; S, 9.35; Cl, 10.34; Sulfated Ash, 20.72; $H_2O$, O;

Less on drying in vacuum at 100° C., O. Found: C, 48.85; H, 2.39; N, 8.22; S, 9.54; Cl, 10.43; Sulfated Ash, 20.58; $H_2O$, 0.07; Loss on drying in vacuum at 100° C., 0.07.

In marked contrast to the hydrated form, which is orange in color, the present anhydrous sodium salt is yellow.

Samples of the hydrated form (Preparation 1) and the present anhydrous form were reduced to a fine particle size and compacted into tablets in a ½ inch diameter die at a final pressure of 2000 lb. In each case, the punch was removed and that end of the die covered by parafilm in order to permit testing of dissolution rate from a single flat surface of known surface area. The die containing the compressed drug was placed in the bottom of a USP dissolution flask with paddle 2.5 cm. above the exposed drug surface. At 25° C., both in $H_2O$ and in 0.05M borate buffer at pH 9.0, the intrinsic dissolution rate (which can be an important factor in the efficacy of oral dosage forms) was approximately three times faster for the anhydrous form than for the hydrate.

The anhydrous form shows little tendency to reform the hydrate. Even in a water wet granulation employed below in the preferred preparation of capsules, the hydrate was not formed (as evidenced by a lack of color change from yellow towards orange).

EXAMPLE 2

Oral Capsule Dosage Form Containing the Anhydrous Sodium of 5-chloro-3-(2-thenoyl)-2-oxindole-1-carboxamide The following ingredients were blended, wet granulated with 875 ml. of water and finally dried to 5% water by Karl Fischer:

| | |
|---|---|
| Sodium salt of 5-chloro-3-(2-thenoyl)-2-oxindole-1-carboxamide | 600.00 g. (561.52 g.A*) |
| Microcrystalline cellulose (Avicel PH101) | 885.75 g. |
| Hydrated corn starch | 236.25 g. |
| Povidone (PVC-30) | 105.00 g. |

(*A refers to the activity equivalent as free acid)

The dried, wet granulated powder was then further blended with:

| | |
|---|---|
| Sodium starch glycolate (Explotab) | 210.00 g. |
| Magnesium stearate | 42.00 g. |
| Sodium lauryl sulfate | 21.00 g. |

Soft gelatin capsules containing 100 mg.A were prepared on a conventional capsule filling machine, using a fill weight of 375 mg. of the finished blend. These capsules demonstrated excellent bioavailability when orally dosed in dogs, showing by blood levels a high 89% bioavailability relative to an orally dosed solution.

We claim:

1. Anhydrous, crystalline sodium salt of 5-chloro-3-(2-thenoyl)-2-oxindole-1-carboxamide.

2. A pharmaceutical composition for oral use in man comprising an analgesic or antiinflammatory effective amount of the salt of claim 1 and a pharmaceutically acceptable carrier or diluent.

3. A method of orally treating pain or inflammatory conditions in man which comprises administering an analgesic or antiinflammatory effective amount of the salt of claim 1.

* * * * *